United States Patent [19]

LeGrow et al.

[11] Patent Number: 5,679,822
[45] Date of Patent: Oct. 21, 1997

[54] HIGH PURITY BRANCHED PHENYLSILOXANE FLUIDS

[75] Inventors: Gary E. LeGrow, Newberry; William I. Latham, III, Gainesville, both of Fla.

[73] Assignee: PCR, Inc., Gainesville, Fla.

[21] Appl. No.: 789,277

[22] Filed: Jan. 28, 1997

[51] Int. Cl.$^6$ .................................................. C07F 7/08
[52] U.S. Cl. ........................................ 556/455; 556/456
[58] Field of Search .................................. 556/456, 455

[56] References Cited

U.S. PATENT DOCUMENTS

| | | | |
|---|---|---|---|
| 2,899,404 | 8/1959 | Lewis | 556/456 |
| 3,978,104 | 8/1976 | Razzano | 260/448.2 |
| 4,206,289 | 6/1980 | Meiners et al. | 521/110 |
| 4,281,147 | 7/1981 | Koerner et al. | 556/459 |
| 5,039,518 | 8/1991 | Barone et al. | 424/63 |
| 5,179,185 | 1/1993 | Yamamoto et al. | 528/32 |

FOREIGN PATENT DOCUMENTS 1050915   12/1966   United Kingdom .

OTHER PUBLICATIONS

Chemical Abstracts, vol. 55, 17579–80, German Patent No. 1,046,049, 1961.

Chemical Abstracts, 1961, 14382, GB 848,719, 1961.

Chemical Abstracts, vol. 45, 10676, US 2,567,100, 1955.

Cosmetic Ingredient Dictionary, Monographs, p. 757, Feb. 1981.

CTFA International Buyers' Guide, Ingredients and Suppliers, p. 166, Dec. 1980.

Dow Corning 556 Cosmetic Grade Silicone Fluid Product Data Sheet, Jan. 1983.

*Primary Examiner*—Paul F. Shaver
*Attorney, Agent, or Firm*—Hedman, Gibson & Costigan, P.C.

[57] ABSTRACT

The invention provides high purity branched phenylsilsesquioxane containing fluids of the general formula Me$_3$SiO—(Me$_3$SiOPhSiO)$_x$—SiMe$_3$, wherein Me is methyl, Ph is phenyl, and x is 1 to 6, and an essentially zero waste process for their synthesis in quantitative yield.

17 Claims, No Drawings

HIGH PURITY BRANCHED PHENYLSILOXANE FLUIDS

FIELD OF THE INVENTION

The present invention relates to high purity branched phenylsilsesquioxane containing fluids and a method for their preparation. More specifically, the present invention relates to neutral branched phenylsilsesquioxane fluids which are substantially free of impurities.

As used throughout the present specification, the abbreviation Me stands for methyl and the abbreviation Ph stands for phenyl.

BACKGROUND OF THE INVENTION

Phenyl-containing silicone polymers with high refractive indices are known to have some dimethylsiloxane-like properties, organic compatibility and chemical stability to strong media. Phenylsilsesquioxane fluids are useful for incorporation into cosmetic formulations, without any chemical reactions, to provide silicone benefits without emulsification. An example of such a use is described in Barone et al., U.S. Pat. No. 5,039,518.

Simmler, German Patent No. 1,046,049 disclosed a method of producing branched phenylsiloxanes by addition of a stoichiometric amount of water into a mixture of trimethylchlorosilane and phenyltrichlorosilane with vigorous stirring. During the latter part of this reaction hydrogen chloride gas was evolved and the reaction mixture dropped below room temperature (endothermic). After neutralization with sodium carbonate, filtration of salts, and vacuum distillation, four products were identified in an 80.5% total yield. The products were 33.8% tris(trimethylsiloxy)phenylsilane, 27.5% tetrakis(trimethylsiloxy)-1,3-diphenyldisiloxane, 6.7% pentakis(trimethylsiloxy)-1,3,5-triphenyltrisiloxane, and 12.5% hexakis(trimethylsiloxy)-1,3,5,7-tetraphenyltetrasiloxane. Calculations, made using the above data, indicate that this total product mixture possesses a 2.22 $Me_3Si/PhSi$ ratio, suggesting that the majority of the unaccounted for yield (19.5%) may be $Me_3Si$ species which is lost to the environment during the hydrolysis reaction.

The chemical formula $Me_3SiO—(Me_3SiOPhSiO)_n—SiMe_3$ is used to describe the chemical composition of phenyl trimethicone by the Cosmetics, Toiletries and Fragrances Association (CTFA) in their International Cosmetic Dictionary, Sixth Edition, Volume 1, page 757 (1995). Suppliers of this chemical include, but are not limited to, Dow Corning Corporation and General Electric Company. In a product data sheet (Form 22-24-242D-85) for Dow Corning 556 Cosmetic-Grade Silicone Fluid, the chemical formula of the product is depicted as $Me_3SiO—(Me_3SiOPhSiO)_n—SiMe_3$.

Analysis of samples of these two commercially available materials indicated the presence of methoxy groups on silicon. The presence of these methoxy groups suggests that either methoxysilane or methanol or both were involved in the synthesis of these products. Additionally, the presence of methoxy groups on silicon will generally result in the formation of methanol upon contact with water due to hydrolysis of the Si—OMe groups. The presence of these methoxy or alkoxy groups is undesirable both from a potential chemical instability standpoint, as well as from an enduse standpoint in the personal care products industry.

Other impurities which need to be avoided in branched phenylsilsesquioxane fluids are compounds with silanol functionality and chlorosilanes. The presence of compounds with silanol functionality are deleterious from a stability standpoint, i.e., they have poor shelf life stability experiencing viscosity drift and becoming hazy in appearance. Chlorosilanes are undesireable because they are not neutral.

Accordingly, it would constitute a significant advance in the state of the art if a neutral phenylsilsesquioxane fluid having a high refractive index could be prepared which contained substantially no detectable silanol (SiOH), substantially no detectable alkoxysilane (SiOR where R is a monovalent hydrocarbon substituent), substantially no detectable chlorosilane, and was also substantially free of free organic and inorganic compounds.

SUMMARY OF THE INVENTION

The present invention provides a high purity branched phenylsilsesquioxane fluid of the general formula $Me_3SiO—(Me_3SiOPhSiO)_x—SiMe_3$ wherein Me is methyl, Ph is phenyl and x is from 1 to about 6 and wherein the phenylsilsesquioxane fluid is substantially free of alkoxysilanes, chlorosilanes, silanol functionalities, and free organic and inorganic compounds.

The present invention also provides a method for producing high purity branched phenylsilsesquioxane fluids, the process comprising the steps of (i) hydrolyzing a mixture of pure trimethylchlorosilane and pure phenyltrichlorosilane with sufficient water to produce a reaction mixture of a silicone reaction intermediate in an aqueous layer not in excess of 25 weight percent hydrochloric acid, at a temperature of up to 90° C.; (ii) washing residual acid from the aqueous layer; (iii) azeotropically removing water from the silicone reaction intermediate; and (iv) trimethylsilylating the silanol groups in the silicone reaction intermediate in the presence of at least a stoichiometric amount of hexamethyldisiloxane and an acid catalyst.

DETAILED DESCRIPTION OF THE PRESENT INVENTION

The present invention provides a novel branched phenylsilsesquioxane fluid of the general formula:

wherein Me is methyl, Ph is phenyl and x is from 1 to about 6, which fluid is characterized in that it is substantially, and preferably completely, free of detectable amounts of silanol, alkoxysilane, chlorosilane, and other organic and inorganic impurities.

The high purity branched phenylsilsesquioxane fluids of the present invention can be prepared by a novel two step process. In the first step, a mixture of trimethylchlorosilane and phenyltrichlorosilane, in a molar ratio ranging from about 5:1 to about 1:1 are hydrolyzed with a stoichiometric excess of distilled water which produces an aqueous layer not exceeding 25 weight percent, preferably less than 18 weight percent, of hydrochloric acid.

The trimethylchlorosilane and phenyltrichlorosilane reactants are available commercially or may be produced by methods known to those skilled in the art. In a preferred embodiment, substantially pure to completely pure reactants are employed in the process of the present invention.

The co-hydrolysis reaction of the first step of the method of the present invention may be carried out over a range of temperatures of from about ambient to about 90° C., preferably from about ambient to about 80° C., and more preferably from about ambient to about 60° C. The reactor is preferably also equipped with a cold water condenser, capable of preventing the loss of any volatile silane species, including but not limited to trimethylchlorosilane.

After the co-hydrolysis reaction is complete, the acid layer is separated from the silicone layer. The silicone layer is washed free of residual acid, by any of the methods known to those of ordinary skill in the art. The silicone layer is then heated to 100° C., at which point water and hexamethyldisiloxane co-volatilize. Free water is then azeotropically removed from the silicone layer. Hexamethyldisiloxane which has volatilized is returned to the silicone layer after substantially all of the free water has been removed.

At this stage of the process the chemical composition of the silicone layer can be described by the following general formula:

Me₃SiO(Me₃SiOPhSiO)_x(HOPhSiO)_ySiMe₃ wherein Me is methyl, Ph is phenyl, x is from 0 to 6, and y is from 0 to 6. This includes species wherein both x and y are 0, i.e., species of the formula Me₃SiOSiMe₃, or hexamethyldisiloxane, which is present as a result of homo-hydrolysis of trimethylchlorosilane, as opposed to the co-hydrolysis of trimethylchlorosilane and phenyltrichlorosilane. Hexamethyldisiloxane is a necessary reactant for the second step of the process of the present invention.

In the second step of the process of the present invention, the silicone layer, at ambient temperature, is catalyzed with an acidic catalyst, such as 0.1% by weight of trifluoromethanesulfonic acid. Other catalysts contemplated for use in the present invention are any of the non-chlorine containing acids such as sulfuric acid and nitric acid.

The silicone layer is then stirred and heated at up to about 50° C. for a sufficient time to replace all residual SiOH (silanol) groups with SiOSiMe₃ groups. The completion of this reaction may readily be monitored by gas layer chromatography as is well known to those of ordinary skill in the art.

After completion of the reaction, the acid catalyst is neutralized with a salt, and the salt is filtered from the reaction mixture. A wide variety of salts may be employed to neutralize and filter the acid catalyst. Exemplary of the salts useful in the practice of the present invention are magnesium sulfate, calcium carbonate, calcium bicarbonate and the like. The remaining silicone material is then stripped to remove any residual hexamethyldisiloxane to provide the high purity branched phenylsilsesquioxane containing fluids of the present invention.

A wide range of branched trimethylsilylated phenylsilsesquioxane fluids can be produced in accordance with the present invention with refractive indices ranging from below about 1.4400 (25° C.) to greater than about 1.4900 (25° C.), with corresponding viscosities ranging from about 5.0 cs (25° C.) to greater than about 500 cs (25° C.) by varying the molar ratio of trimethylchlorosilane to phenyltrichlorosilane.

In an especially preferred embodiment, the residual hexamethyldisiloxane removed in the stripping step of the second process step of the present invention may be recycled to the initial reaction mixture. In such an embodiment, the amount of trimethylchlorosilane in the initial reaction mixture is reduced by the amount of hexamethyldisiloxane recycled, with a corresponding decrease in the amount of distilled water needed for hydrolysis and to maintain the hydrochloric acid concentration in the acid layer constant. In this manner, the present invention further provides a process which is essentially a zero waste process with respect to organosilicon chemicals.

DESCRIPTION OF THE PREFERRED EMBODIMENTS

The following examples illustrate the present invention. They are not to be construed to limit the scope of the appended claims in any manner whatsoever.

Example 1

A mixture of 325.5 g (3.0 mole) of pure trimethylchlorosilane and 211.5 g (1.0 mole) of pure phenyltrichlorosilane was slowly added, with stirring, from an addition funnel to a 2 liter 3 necked round bottom flask equipped with a mechanical stirrer and blade, thermometer and cold water condenser, and containing 1051 g (58.4 mole) of distilled water. The rate of addition was controlled to prevent the temperature of the reaction mixture from exceeding 60° C. After the addition was complete, the contents of the flask were allowed to cool to 40° C. The lower aqueous layer was removed from the flask and 1000 g of distilled water were introduced and rapidly stirred and mixed with the upper silicone layer to reduce its acid content. The stirrer was stopped and the two layers were allowed to separate, whereupon the lower acid layer was again removed. This water washing operation was repeated three more times until the pH of the upper layer was in excess of 6. The silicone layer was heated to 100° C. causing hexamethyldisiloxane and water to co-distill. Water was azeotropically removed from the silicone fluid in this manner until no more water was formed. The hexamethyldisiloxane was returned to the flask. Six drops of pure trifluoromethane sulfonic acid were added to the silicone layer. This mixture was stirred at room temperature for 24 hours. While continuing the stirring, ten grams of anhydrous magnesium sulfate were added to the flask. After an additional hour of stirring, the silicone layer was filtered. The product mixture weighted 370 g (99.5% theory). NMR analysis of this mixture showed the Me₃Si/PhSi ratio to be 3.0. The silicone layer was stripped under vacuum at room temperature. This process removed 56 g (15 percent by weight) of hexamethyldisiloxane. The remaining product weighed 314 g (84% yield) and was composed of 53% tris(trimethylsiloxy)phenylsilane, 27% tetrakis(trimethylsiloxy)-1,3-diphenyldisiloxane and 20% higher oligomers, by uncalibrated GC analysis. This product has a refractive index of 1.4550 (25° C.) and a viscosity of 12.6 cs (25° C.), and was neutral, colorless and odorless.

Example 2

A mixture of 434.0 g (4.0 mole) of pure trimethylchlorosilane and 211.5 g (1.0 mole) of phenyltrichlorosilane was slowly added, with stirring, from an addition funnel to a 3 liter 3 necked round bottom flask equipped with a mechanical stirrer and blade, thermometer and cold water condenser, and containing 1227 g (68.2 mole) of distilled water. The rate of addition was controlled to prevent the temperature of the reaction mixture from exceeding 60° C. After the addition was complete, the contents of the flask were allowed to cool to 40° C. The lower aqueous acid layer was removed from the flask and 1200 g of distilled water were introduced and rapidly stirred and mixed with the upper silicone layer to reduce its acid content. The stirrer was stopped and the two layers were allowed to separate, whereupon the lower acid layer was again removed. This water washing operation was repeated three more times until the pH of the upper layer was in excess of 6. The silicone layer was heated to 100° C. causing hexamethyldisiloxane and water to co-distill. Water was azeotropically removed from the silicone fluid in this manner until no more water was formed. The hexamethyldisiloxane was returned to the flask. Six drops of pure trifluoromethanesulfonic acid were added to the silicone layer. This mixture was stirred at room temperature for 18 hours. While continuing the stirring, ten grams of anhydrous magnesium sulfate were added to the flask. After an additional hour of stirring, the silicone layer was filtered. The product mixture weighed 445 g (98% theory). NMR analysis of this mixture showed the $Me_3Si/PhSi$ ratio to be 4.0. The silicone layer was stripped under vacuum at room temperature. This process removed 95 g (21.0% weight) of hexamethyldisiloxane. The remaining product weighed 350 g (77% yield) and was composed of 60% tris(trimethylsiloxy) phenylsilane, 18% tetrakis(trimethylsiloxy)-1,3-diphenyldisiloxane, and 22% higher oligomers, by uncalibrated GC analysis. This product had a refractive index of 1.4530 (25° C.) and a viscosity of 9.6 cs (25° C.), and was neutral, colorless and odorless.

Example 3

A mixture of 108.5 g (1.0 mole) of pure trimethylchlorosilane and 211.5 g (1.0 mole) of phenyltrichlorosilane was slowly added, with stirring, from an addition funnel to a 2 liter 3 necked round bottom flask equipped with a mechanical stirrer and blade, thermometer and cold water condenser, and containing 701 g (39.0 mole) of distilled water. The rate of addition was controlled to prevent the temperature of the reaction mixture from exceeding 60° C. After the addition was complete, the contents of the flask were allowed to cool to 40° C. The lower aqueous acid layer was removed from the flask and 700 g of distilled water were introduced and rapidly stirred and mixed with the upper silicone layer to reduce its acid content. The stirrer was stopped and the two layers were allowed to separate, whereupon the lower acid layer was again removed. This water washing operation was repeated three more times until the pH of the upper layer was in excess of 6. The silicone layer was heated to 100° C. causing hexamethyldisiloxane and water to co-distill. Water was azeotropically removed from the silicone fluid in this manner until no more water was formed. The hexamethyldisiloxane was returned to the flask. Six drops of pure trifluoromethanesulfonic acid were added to the silicone layer. This mixture was stirred at room temperature for 24 hours. While continuing the stirring, ten grams of anhydrous magnesium sulfate were added to the flask. After an additional hour of stirring, the silicone layer was filtered. The product mixture weighed 206 g (98% theory). NMR analysis of this mixture showed the $Me_3Si/PhSi$ ratio to be 1.0. The silicone layer was stripped under vacuum at room temperature. This process removed 10 g (5.0% weight) of hexamethyldisiloxane. The remaining product weighed 195 g (93% yield) and was composed of 32% tris(trimethylsiloxy) phenylsilane, 22% tetrakis(trimethylsiloxy)-1,3-diphenyldisiloxane, and 46% higher oligomers, by uncalibrated GC analysis. This product had a refractive index of 1.4929 (25° C.) and a viscosity of 530 cs (25° C.), and was neutral, colorless and odorless.

Example 4

A mixture of 217.0 g (2.0 mole) of pure trimethylchlorosilane and 81.0 g (0.5 mole) of hexamethyldisiloxane and 211.5 (1.0 mole) of phenyltrichlorosilane was slowly added, with stirring, from an addition funnel to a 2 liter 3 necked round bottom flask equipped with a mechanical stirrer and blade, thermometer and cold water condenser, and containing 877 g (48.7 mole) of distilled water. The rate of addition was controlled to prevent the temperature of the reaction mixture from exceeding 60° C. After the addition was complete, the contents of the flask were allowed to cool to 40° C. The lower aqueous acid layer was removed from the flask and 900 g of distilled water were introduced and rapidly stirred and mixed with the upper silicone layer to reduce its acid content. The stirrer was stopped and the two layers were allowed to separate, whereupon the lower acid layer was again removed. This water washing operation was repeated three more times until the pH of the upper layer was in excess of 6. The silicone layer was heated to 100° C. causing hexamethyldisiloxane and water to co-distill. Water was azeotropically removed from the silicone fluid in this manner until no more water was formed. The hexamethyldisiloxane was returned to the flask. Six drops of pure trifluoromethanesulfonic acid were added to the silicone layer. This mixture was stirred at room temperature for 24 hours. While continuing the stirring, ten grams of anhydrous magnesium sulfate were added to the flask. After an additional hour of stirring, the silicone layer was filtered. The product mixture weighed 365 g (98% theory). NMR analysis of this mixture showed the $Me_3Si/PhSi$ ratio to be 3.0. The silicone layer was stripped under vacuum at room temperature. This process removed 59 g (16.0% weight) of hexamethyldisiloxane. The remaining product weighed 306 g (82% yield) and was composed of 52% tris(trimethylsiloxy) phenylsilane, 28% tetrakis(trimethylsiloxy)-1,3-diphenyldisiloxane, and 20% higher oligomers, by uncalibrated GC analysis. This product had a refractive index of 1.4555 (25° C.) and a viscosity of 12.7 cs (25° C.), and was neutral, colorless and odorless.

Example 5

A 300 g sample of the product of Example 2 was distilled under vacuum to yield 175 g (58% yield) of greater than 99.8% pure (by capillary GC analysis) tris(trimethylsiloxy) phenylsilane, bp 100° C. (1 mm), Refractive Index 1.4371 (25° C.) and viscosity 5.0 cs (25° C.).

Comparative Example 1

A mixture of 325.5 g (3.0 mole) of pure trimethylchlorosilane and 211.5 g (1.0 mole) of phenyltrichlorosilane was added to 108 g (6.0 mole—100% excess) of distilled water with vigorous stirring. Initially, this reaction was exothermic; however, at the point where the aqueous layer becomes saturated in hydrogen chloride, the reaction becomes endothermic with the formation of hydrogen chloride gas. The evolving hydrogen chloride gas entrains trimethylchlorosilane, which is readily observed when the gas stream is quenched in an ice water bath, because of the formation of two phases. NMR analysis of the silicon product of this reaction showed the $Me_3Si/PhSi$ ratio to be 2.25, indicating that 25% of the initial trimethylchlorosilane fed to the reactor was lost due to entrainment by hydrogen chloride gas.

Comparative Example 2

A mixture of 325.5 g (3.0) mole of pure trimethylchlorosilane and 211.5 g (1.0 mole) of phenyltrichlorosilane was slowly added, with stirring, from an addition funnel to a 3 liter 3 necked round bottom flask equipped with a mechanical stirrer and blade, thermometer and cold water condenser, and containing 1270 g (70.6 mole) of distilled water. The rate of addition was controlled to prevent the temperature of the reaction mixture from exceeding 60° C. After the addition was complete, the contents of the flask were allowed to cool to 40° C. The lower aqueous acid layer was removed from the flask and 1200 g of distilled water were introduced and rapidly stirred and mixed with the upper silicone layer to reduce its acid content. The stirrer was stopped and the two layers were allowed to separate, whereupon the lower acid layer was again removed. This water washing operation was repeated three more times until the pH of the upper layer was in excess of 6. The silicone layer was heated to 100° C. causing hexamethyldisiloxane and water to co-distill. Water was azeotropically removed from the silicone fluid in this manner until no more water was formed. The hexamethyldisiloxane was returned to the flask. GC analysis of the product mixture at this point showed the presence of the expected products, hexamethyldisiloxane, tris(trimethylsiloxy)phenylsilane, tetrakis(trimethylsiloxy)-1,3-diphenyldisiloxane, pentakis(trimethylsiloxy)-1,3,5-triphenyltrisiloxane, and higher oligomers. However, in addition there were smaller peaks (up to 25% of the main peak) present just before each of the phenyl containing siloxane peaks. By GC/MS analysis these peaks were identified as silanol functional materials where a trimethylsiloxy substituent is missing, replaced by a silanol group, e.g., bis(trimethylsiloxy)phenylsilanol, 1,3,3-tris(trimethylsiloxy)-1,3-diphenyldisiloxan-1-ol, and 1,1,5,5-tetrakis(trimethylsiloxy)-1,3,5-triphenyltrisiloxan-3-ol (or an isomer thereof).

Many variations of the present invention will suggest themselves to those skilled in the art in light of the above-detailed description. For example, the molar ratio of trimethylchlorosilane and phenyltrichlorosilane may be varied between 1 and 6. Additionally, acid catalysts other than trifluoromethanesulfonic acid may be employed. All such obvious modifications are within the full intended scope of the appended claims.

I claim:

1. A high purity, neutral, colorless and odorless branched phenylsilsesquioxane fluid of the general formula:

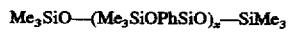

wherein Me is methyl, Ph is phenyl and x ranges from 1 to about 6, said fluid being substantially free of alkoxy silane, chlorosilane, silanol functionality, hexamethyldisiloxane and free organic and/or inorganic compounds.

2. A high purity branched phenylsilsesquioxane fluid as defined in claim 1 wherein x ranges from 1 to 3.

3. A high purity branched phenylsilsesquioxane fluid as defined in claim 2 wherein x is 1.

4. A high purity branched phenylsilsesquioxane fluid as defined in claim 1 which is 99.9% pure.

5. A high purity branched phenylsilsesquioxane fluid as defined in claim 1 which contains no detectable alkoxysilane, chlorosilane, silanol functionality, hexamethyldisiloxane, free organics, and free inorganics.

6. A silicone fluid consisting of phenyltris(trimethylsiloxy)silane.

7. A process for the production of a high purity branched phenylsilsesquioxane fluid of the general formula

wherein Me is methyl, Ph is phenyl, and x ranges from 1 to about 6, having a purity of greater than 99.9% and substantially free of alkoxysilane, chlorosilane, silanol functionality, hexamethyldisiloxane, free organic compounds and free inorganic compounds, said process comprising the steps of:

(a)(i) hydrolyzing a mixture of pure trimethylchlorosilane and pure phenyltrichlorosilane with distilled water in an amount sufficient to produce an aqueous layer of less than about 25 weight percent hydrochloric acid, maintaining the temperature of the hydrolysis reaction mixture below about 90° C., to form a silicone reaction intermediate;

(ii) washing residual acid from the silicone reaction intermediate; and (iii) azeotropically removing water from the washed silicone reaction intermediate to produce a dried silicone reaction intermediate; and (b) trimethylsilylating the silanol groups in the dried silicone reaction intermediate with at least a stoichiometric amount of hexamethyldisiloxane in the presence of an acid catalyst.

8. A process as defined in claim 7 wherein a said trimethylsilylating step is carried out with a two fold excess of the stoichiometric amount of hexamethyldisiloxane.

9. A process as defined in claim 7 wherein said hydrolyzing step is carried out at a temperature below about 60° C.

10. A process as defined in claim 7 wherein said hydrolysis step is carried out with distilled water in an amount sufficient to produce an aqueous layer of from about 15 to about 18 weight percent hydrochloric acid.

11. A process as defined in claim 7 wherein hexamethyldisiloxane is present both at the beginning and the end of the trimethylsilylating step.

12. A process as defined in claim 7 wherein said acid catalyst comprises trifluoromethanesulfonic acid.

13. A process as defined in claim 7 wherein said acid catalyst is neutralized and the salt filtered after completion of the trimethylsilylation reaction.

14. A process as defined in claim 11 wherein excess hexamethyldisiloxane present at the end of the trimethylsilylating step is removed from the product by stripping.

15. A process as defined in claim 14 wherein said removed hexamethyldisiloxane is recycled to the hydrolysis reaction mixture.

16. A process as defined in claim 11 wherein said washing step is performed to provide a silicone reaction intermediate having a pH of at least 6.

17. A high purity branched phenylsilsesquioxane fluid produced by the process as defined in claim 7.

* * * * *